US012576582B2

(12) United States Patent　　(10) Patent No.:　US 12,576,582 B2

Hamoudi et al.　　(45) Date of Patent:　　Mar. 17, 2026

(54) VAPOR-BASED METHOD AND SYSTEM FOR PRINTING A 3D STRUCTURE

(71) Applicant: Qatar Foundation for Education, Science and Community Development, Doha (QA)

(72) Inventors: Hicham Hamoudi, Doha (QA); Golibjon Berdiyorov, Doha (QA)

(73) Assignee: HAMAD BIN KHALIFA UNIVERSITY, Doha (QA)

( * ) Notice:　Subject to any disclaimer, the term of this patent is extended or adjusted under 35 U.S.C. 154(b) by 0 days.

(21) Appl. No.: 18/217,219

(22) Filed:　Jun. 30, 2023

(65)　　　　Prior Publication Data

US 2023/0356462 A1　　Nov. 9, 2023

Related U.S. Application Data

(62) Division of application No. 16/876,785, filed on May 18, 2020, now Pat. No. 11,718,023.

(51) Int. Cl.
　　*B29C 64/209*　　　(2017.01)
　　*B29C 64/106*　　　(2017.01)
　　　　　(Continued)

(52) U.S. Cl.
　　CPC .......... *B29C 64/159* (2017.08); *B29C 64/106* (2017.08); *B29C 64/209* (2017.08); (Continued)

(58) Field of Classification Search
　　CPC ... B29C 64/159; B29C 64/245; B29C 64/295; B29C 64/209; B29C 64/106; (Continued)

(56)　　　　References Cited

U.S. PATENT DOCUMENTS

2005/0253139 A1*　11/2005　Gorman ................. B82Y 30/00
　　　　　　　　　　　　　　　　　　257/46
2008/0257187 A1　10/2008　Millward
　　　　　　　　(Continued)

OTHER PUBLICATIONS

Hamoudi, "Going beyond the self-assembled monolayer: metal intercalated dithiol multilayers and their conductance", RSC Adv., 2014, 4, 39657 accessed at https://pubs.rsc.org/en/content/articlelanding/2014/ra/c4ra05476h on Sep. 4, 2025. (Year: 2014).*

(Continued)

*Primary Examiner* — JaMel M Nelson

(74) *Attorney, Agent, or Firm* — K&L Gates LLP

(57)　　　　ABSTRACT

A vapor-based method and system for printing a 3D structure are provided. The vapor-based method includes providing a substrate; providing a first vapor including an organic molecule including a functional group at each end for creation of self-assembled monolayers (SAMs) as a building block for printing the 3D structure; providing a second vapor including metal ions; applying the first vapor and the second vapor to form molecular-metal SAMs thereby providing a multiple layered SAMs material on the substrate; and applying a force and forming the 3D structure from the multiple layered SAMs material, wherein the 3D structure is provided on the substrate.

9 Claims, 13 Drawing Sheets
(8 of 13 Drawing Sheet(s) Filed in Color)

(51) Int. Cl.

| | |
|---|---|
| *B29C 64/159* | (2017.01) |
| *B29C 64/245* | (2017.01) |
| *B29C 64/295* | (2017.01) |
| *C07C 321/04* | (2006.01) |
| *C07C 321/26* | (2006.01) |
| *C07D 213/70* | (2006.01) |
| *B33Y 10/00* | (2015.01) |
| *B33Y 30/00* | (2015.01) |

(52) U.S. Cl.
CPC .......... *B29C 64/245* (2017.08); *B29C 64/295* (2017.08); *C07C 321/04* (2013.01); *C07C 321/26* (2013.01); *C07D 213/70* (2013.01); *B33Y 10/00* (2014.12); *B33Y 30/00* (2014.12)

(58) Field of Classification Search
CPC ... B29C 64/264; B29C 64/268; B29C 64/371; B33Y 10/00; B33Y 30/00; C07D 213/70; C23C 16/4418; C07C 321/26
See application file for complete search history.

(56) References Cited

U.S. PATENT DOCUMENTS

2015/0034008 A1* 2/2015 Jang .................... C23C 16/4401
118/712

2017/0306491 A1* 10/2017 Liang ................ C23C 16/45502
2020/0090924 A1* 3/2020 Wu .......................... H01L 21/32
2020/0216950 A1* 7/2020 Rowe ................ C23C 16/45553
2021/0313228 A1* 10/2021 Nguyen ................ H01L 21/321
2022/0226931 A1* 7/2022 Kotar ................... B23K 26/123

OTHER PUBLICATIONS

Hicham Hamoudi; "Bottom-Up Nanoarchitectonics of Two-Dimensional Freestanding Metal Doped Carbon Nanosheet"; International Center for Materials Nanoarchitectonics (WPI-MANA), National Institute for Materials Science (NIMS) 2, 1-1 Namiki, Tsukuba, 305-0044, Japan; (23 pages).

Hicham Hamoudi, et al; "Going beyond the self-assembled monolayer: metal intercalated dithiol multilayers and their conductance"; RSC Advances; Aug. 2014; (11 pages).

Katsuhiko Ariga, et al; "Self-assembly as a key player for materials nanoarchitectonics"; Science and Technology of Advanced Materials, 20:1, 51-95, DOI: 10.1080/14686996.2018.1553108; (46 pages).

Hicham Hamoudi, et al; Selfassembly of α,ω-dithiols on surfaces and metal dithiol heterostructures; Ann. Phys. (Berlin) 528, No. 3-4, 242-263 (2016); (22 pages).

* cited by examiner

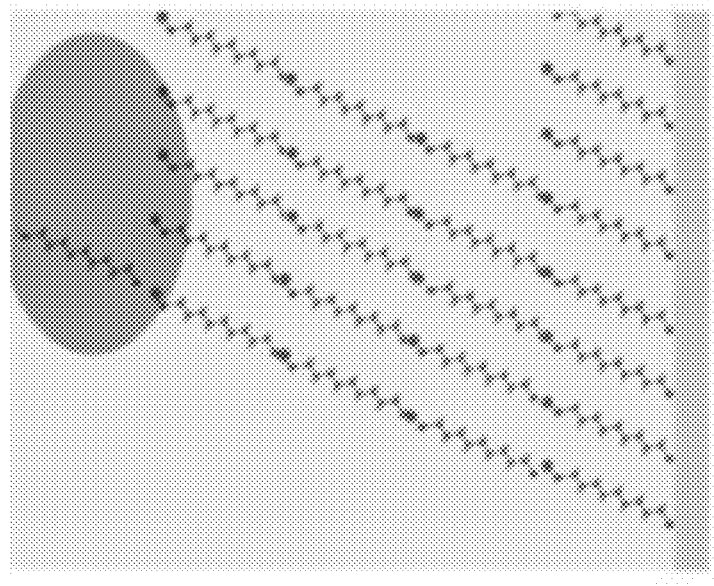
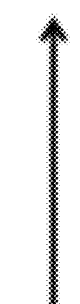
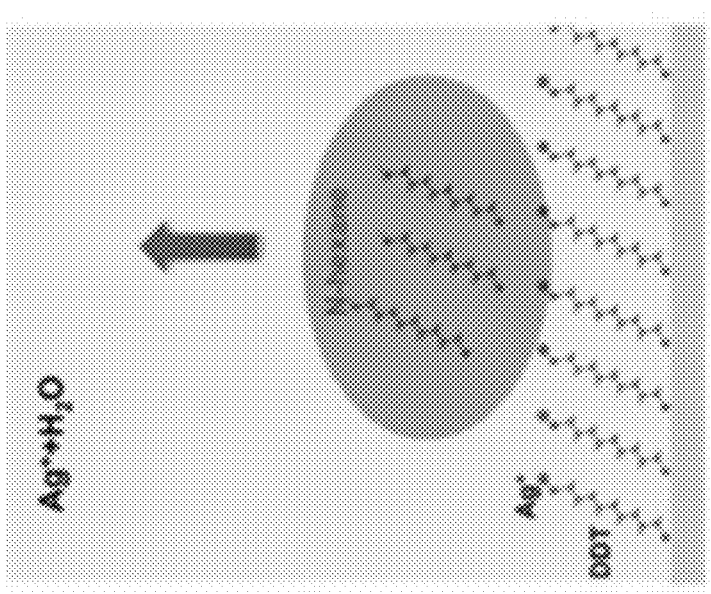
FIG. 4

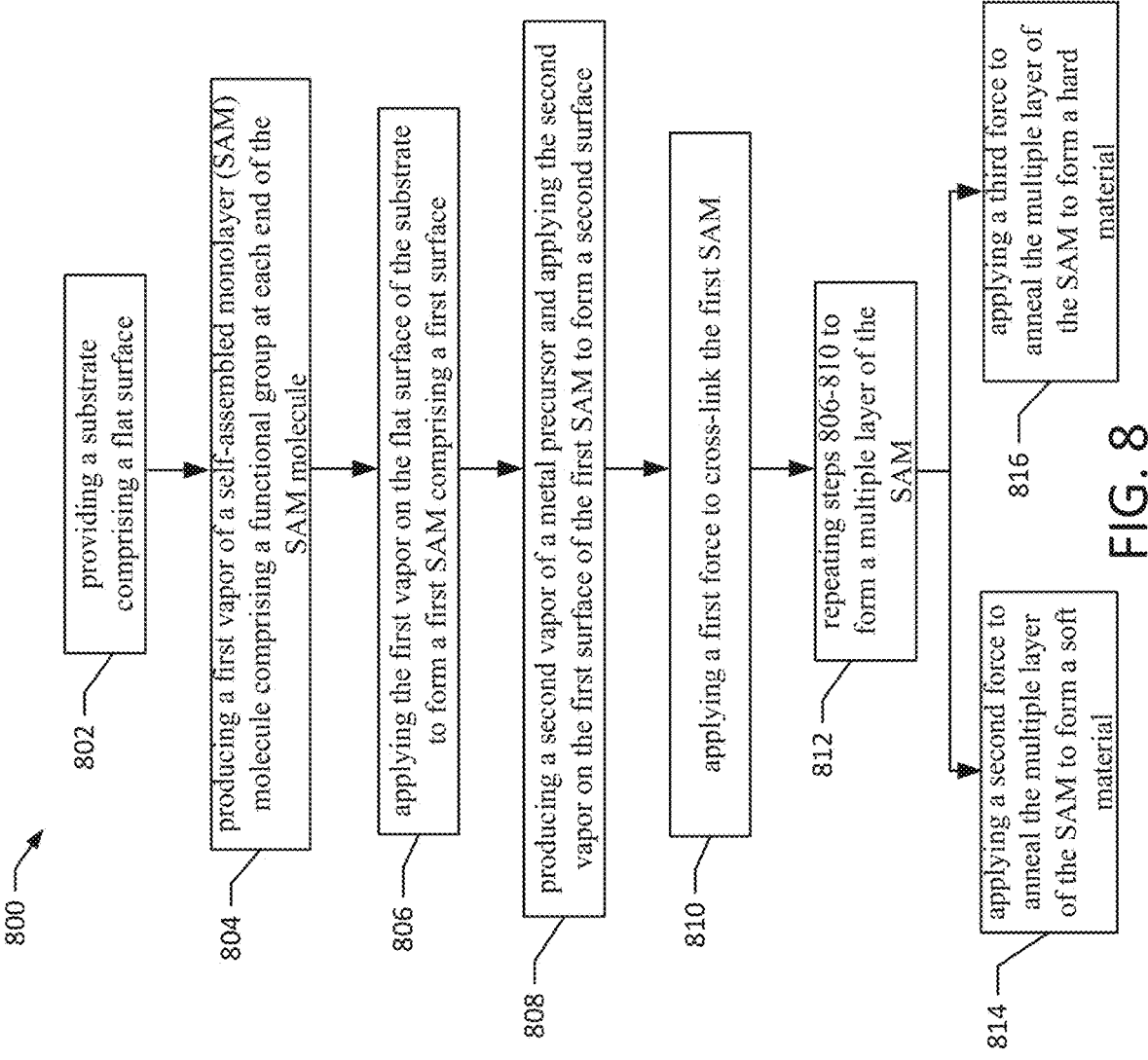

800

802  providing a substrate comprising a flat surface 804  producing a first vapor of a self-assembled monolayer (SAM) molecule comprising a functional group at each end of the SAM molecule 806  applying the first vapor on the flat surface of the substrate to form a first SAM comprising a first surface 808  producing a second vapor of a metal precursor and applying the second vapor on the first surface of the first SAM to form a second surface 810  applying a first force to cross-link the first SAM 812  repeating steps 806-810 to form a multiple layer of the SAM 814  applying a second force to anneal the multiple layer of the SAM to form a soft material 816  applying a third force to anneal the multiple layer of the SAM to form a hard material

FIG. 8

VAPOR-BASED METHOD AND SYSTEM FOR PRINTING A 3D STRUCTURE

CROSS-REFERENCE TO RELATED APPLICATIONS

The present application is Divisional Application of U.S. application Ser. No. 16/876,785, filed on May 18, 2020, the entire contents of which is hereby incorporated by reference.

FIELD OF THE INVENTION

The present disclosure relates to a novel 3D printing method based on molecular self-assembly and a related system for creating low-cost and new type of material for highly ordered materials fabrication and bio-applications.

BACKGROUND

In general, three-dimensional (3D) printing refers to a process of creating complex 3D objects through layer by layer deposition of materials (i.e., additive manufacturing). Many different types of materials can be used for 3D printing, such as polymer and polymer compounds (acrylonitrile butadiene styrene (ABS), polylactic acid (PLA), photopolymers, polycarbonate, pristine polyamide (nylon) and glass filled polyamide, polyethylene terephthalate glycol), stereo-lithography materials (epoxy resins), ceramics, metal and metal complexes (gold, aluminum, silver, titanium and steel).

Among the plastic materials, ABS is the most common material for 3D printing and Fused Deposition Modeling (FDM) is the most suitable technology for 3D object constructions. During the FDM process, such a thermoplastic filament is heated to its melting point and then deposited layer by layer. Direct metal laser sintering (DMLS) and direct metal laser melting (DMLM) are two common technologies for metallic 3D printing. Such printers use a laser beam to melt metal powders which will consequently be deposited on top of each other. However, the processes of melting and post-deposition solidification are time consuming and therefore the speed remains an important issue in 3D printing.

Needed in the art are 3D printing systems and methods for creating low-cost and new type of material for highly ordered materials fabrication and bio-applications.

SUMMARY OF THE INVENTION

According to one non-limiting aspect of the present disclosure, an example embodiment of a solution-based method for 3D printing comprises i) providing a substrate comprising a flat surface; ii) providing a first solution of a self-assembled monolayer (SAM) molecule comprising a functional group at each end of the SAM molecule; iii) applying the first solution to the flat surface of the substrate to form a first SAM comprising a first liquid surface; iv) providing a second solution of a metal precursor; v) applying the second solution on the first liquid surface to form a second liquid surface over the first SAM; vi) applying a first force to cross-link the first SAM; repeating steps iii) and v)-vi) to form a multiple layer of the SAM; and either applying a second force to anneal the multiple layer of the SAM to form a soft material, or alternatively applying a third force to anneal the multiple layer of the SAM to form a hard material.

In one embodiment, the substrate is a metal substrate such as Au.

In one embodiment, the SAM molecule is a dithiol organic molecule.

In one embodiment, the dithiol organic molecule is a dithiol alkane or a dithiol aromatic-based molecule.

In one embodiment, the dithiol alkane is dithiol hexane.

In one embodiment, the dithiol aromatic-based molecule is a dithiol dipyridine or a dithiol dibenene.

In one embodiment, the metal precursor in step iv) is a silver precursor.

In one embodiment, the first force in step vi) is UV light.

In one embodiment, the second force and the third force in step viii) are heat.

In one embodiment, at least one characteristics of the SAM in step iii) is controllable.

In one embodiment, the at least one characteristics of the SAM comprises shape and size.

In one embodiment, the present disclosure relates to a system capable of applying the solution-based method as discussed above to form a 3D printing structure.

According to another non-limiting aspect of the present disclosure, an example embodiment of a vapor-based method for 3D printing comprises a) providing a substrate comprising a flat surface; b) producing a first vapor of a self-assembled monolayer (SAM) molecule comprising a functional group at each end of the SAM molecule; c) applying the first vapor on the flat surface of the substrate to form a first SAM comprising a first surface; d) producing a second vapor of a metal precursor and applying the second vapor on the first surface of the first SAM to form a second surface; e) applying a first force to cross-link the first SAM; f) repeating steps c)-e) to form a multiple layer of the SAM; and g) either applying a second force to anneal the multiple layer of the SAM to form a soft material or applying a third force to anneal the multiple layer of the SAM to form a hard material.

In one embodiment, the substrate is a metal substrate such as Au.

In one embodiment, the SAM molecule is a dithiol organic molecule.

In one embodiment, the dithiol organic molecule is a dithiol alkane or a dithiol aromatic-based molecule.

In one embodiment, the dithiol alkane is dithiol hexane.

In one embodiment, the dithiol aromatic-based molecule is a dithiol dipyridine or a dithiol dibenene.

In one embodiment, the metal precursor in step d) is a silver precursor.

In one embodiment, the first force in step e) is UV irradiation or electrical force.

In one embodiment, the second force and the third force in step g) are heat.

In one embodiment, at least one characteristics of the SAM in step c) is controllable.

In one embodiment, the at least one characteristics of the SAM comprises shape and size.

In one embodiment, the present disclosure relates to a system capable of applying the vapor-based method as discussed above to form a 3D printing structure.

In one aspect, the present disclosure relates to a system for printing a 3D structure.

In one embodiment, the system comprises a metal substrate providing a flat surface for forming the 3D structure; a metallic tip in an electrical communication with the metal substrate and an electric source so that the metallic tip can provide an electrical force to crosslink a self-assembled monolayer (SAM); a first switchable nozzle in a fluid communication with a vapor source for a SAM molecule; a second switchable nozzle in a fluid communication with a vapor source for a metal precursor; and a heat source for annealing the 3D structure.

In one embodiment, the metal substrate is Au.

In one embodiment, the SAM molecule is a dithiol organic molecule.

In one embodiment, the dithiol organic molecule is a dithiol alkane or a dithiol aromatic-based molecule.

In one embodiment, the dithiol alkane is dithiol hexane.

In one embodiment, the dithiol aromatic-based molecule is a dithiol dipyridine or a dithiol dibenene.

In one embodiment, the metal precursor is a silver precursor.

Additional features and advantages are described herein, and will be apparent from the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a set of diagrams showing preparation of C9-dithiol-Ag freestanding sheet by admission of a drop of n-Hexane with C9-dithiol on top of the C9-Ag SAM inside Ag-water solution;

FIG. 8 is systematic diagram showing a method according certain embodiment of the present disclosure.

DETAILED DESCRIPTION OF THE INVENTION

Figure 1:
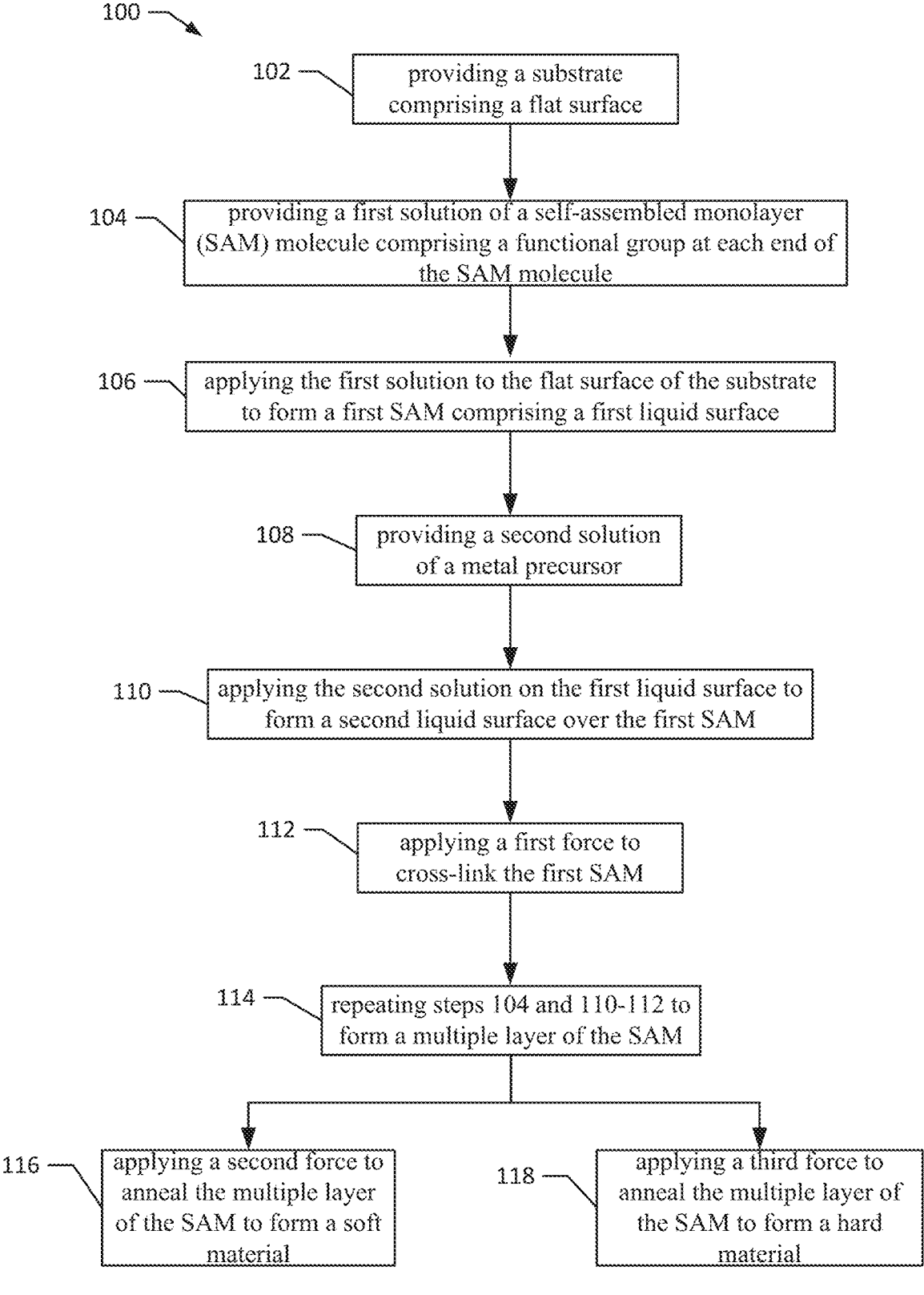
FIG. 1 is systematic diagram showing a method according certain embodiment of the present disclosure.

Unless defined otherwise, all technical and scientific terms used herein have the same meaning as commonly understood by one of ordinary skill in the art to which this invention belongs. As used herein the following terms have the following meanings.

The term "comprising" or "comprises," as used herein, is intended to mean that the compositions and methods include the recited elements, but not excluding others.

The term "about," when used before a numerical designation, e.g., temperature, time, amount, and concentration, including range, indicates approximations which may vary by (+) or (−) 10%, 5% or 1%.

The term "self-assembled monolayer," or "SAM," as used herein, refers to a thin monolayer in which surface active molecules are spontaneously adsorbed on the surface of a particular substrate (e.g., a metal or a metal oxide) to form chemical bonds between the surface active molecules and the substrate. The shape and physical properties of the self-assembled monolayer can be controlled and modified on a molecular level. In one embodiment of the present invention, the SAM comprises self-assembled organic molecules having functional groups (such as thiols) at two ends of the molecule, through which the molecules are adsorbed on a surface of a substrate such as a metal substrate.

In one embodiment, the present disclosure reveals a new concept of fabrication of highly ordered and stable organic and metallic 3D structures. The concept is based on implementing self-assembled monolayer (SAM) molecular building block strategy to layer by layer deposition, where each self-assembled monolayer (SAM) of a specific molecule may separated by metal atoms or clusters.

The stability of each SAM may be ensured by cross-linking the molecules either by UV radiation or voltage biasing. Metallic 3 D structures can also be obtained by annealing the system composed by metallic nanoparticles intercalated with SAMs before cross-linking to evaporate the SAMs.

In one embodiment, the 3D printing can be realized by using either all-solution-based device engineering method, which will radically decrease the fabrication cost, or by molecular vapor deposition technique, which enables more precise control of the resulting 3D structures. Thus, the method (and related systems) may be considered as a new category of 3D printing both in terms of processing and material.

The term "functional group," as used herein, refers to a group that includes one or a plurality of atoms other than hydrogen and sp3 carbon atoms. Examples of functional groups include but are not limited to hydroxyl (—OH), protected hydroxyl, ether (—C—O—C—), ketone (>C=O), ester (—C(=O)O—C—), carboxylic acid (—C(=O)OH), cyano (—C≡N), amido (—C(=O)NH—C—), isocyanate (—N=C=O), urethane (—O—C(=O)—NH—), urea (—NH—C(=O)—NH—), protected amino, thiol (—SH), sulfone, sulfoxide, phosphine, phosphite, phosphate, halide (—X), and the like. In one embodiment, the functional group is a thiol.

The present disclosure, in part, is directed to methods and/or related systems for low-cost and morphologically stable 3D printing. Specifically, the present disclosure is directed to methods and/or related systems for implementing self-assembled phenomenon-based molecular building blocks, the stability of which is obtained by cross-linking the molecules either by UV radiation, or electrons.

In one embodiment, the present disclosure is directed to methods and/or related systems for bottom-up manufacturing of 3D objects through layer-by-layer deposition of molecular SAMs separated by metallic atoms/clusters or nanoparticles.

In one embodiment, the methods and/or related systems allow one to create new 3D complex material structures in a controlled way.

In one embodiment, the present disclosure is directed to either a solution-based method (and related systems) or a vapor-based method (and related systems; e.g., molecular-vapor deposition method and related systems).

Thus, in one specific embodiment, the present disclosure is directed to a solution-based method (and related systems) for 3D printing.

In one embodiment, a solution-based method for 3D printing, comprising the steps of: i) providing a substrate comprising a flat surface; ii) providing a first solution of a self-assembled monolayer (SAM) molecule comprising a functional group at each end of the SAM molecule; iii) applying the first solution to the flat surface of the substrate to form a first SAM comprising a first liquid surface; iv) providing a second solution of a metal precursor; v) applying the second solution on the first liquid surface to form a second liquid surface over the first SAM; vi) applying a first force to cross-link the first SAM; repeating steps iii) and v)-vi) to form a multiple layer of the SAM; and either applying a second force to anneal the multiple layer of the SAM to form a soft material or applying a third force to anneal the multiple layer of the SAM to form a hard material.

Referring now to FIG. 1, an exemplary solution-based method 100 for 3D printing is depicted.

As shown in FIG. 1, a substrate comprising a flat surface is provided (102). In one embodiment, the substrate is a metal substrate. In one embodiment, the metal substrate is gold (Au).

A first solution of a self-assembled monolayer (SAM) molecule comprising a functional group at each end of the SAM molecule is provided (104). In one embodiment, the first solution is made of an organic solvent such as n-hexane.

In one embodiment, the step 102 and the step 104 may be exchanged.

In one embodiment, the functional group is a thiol. In one embodiment, the SAM molecule is a dithiol organic molecule (an organic molecule with two thiols at each end of the molecule).

In one embodiment, the dithiol organic molecule is a dithiol alkane or a dithiol aromatic-based molecule.

In one embodiment, the dithiol alkane is dithiol hexane.

In one embodiment, the dithiol aromatic-based molecule is a dithiol dipyridine or a dithiol dibenene.

Returning back to FIG. 1, the first solution is applied to the flat surface of the substrate to form a first SAM comprising a first liquid surface (106). A first SAM is produced on the flat surface of the substrate.

In one embodiment, the substrate such as a metal substrate (e.g., Au) is immersed in the first solution with an organic solvent such as n-hexane so that the SAM molecules of the first solution form the first SAM on the flat surface of the substrate.

Alternatively, the first solution may be applied to the flat surface of the substrate to form a first SAM comprising a first liquid surface by other means such as physical vapor deposition techniques, electrodeposition or electroless deposition.

In one embodiment, the first solution may be dropped to the flat surface of the substrate to form the first SAM comprising a first liquid surface.

In one embodiment, SAMs may be allowed to form over 12 to 72 hours at room temperature. In one embodiment, SAMs of alkanethiolates may form within minutes.

In one embodiment, one of the two functional groups of the SAM molecule of the first SAM is immobilized on the flat surface of the substrate.

As shown in FIG. 1, a second solution of a metal precursor is provided (108). In one embodiment, the second solution is a silver precursor. In one embodiment, the second solution provides metallic particles or atoms to which the other functional group of the SAM molecule of the first SAM is attached.

In one embodiment, the second solution is applied on the first liquid surface to form a second liquid surface over the first SAM (110). The metallic particles or atoms from the second solution are attached by the other functional group of the SAM molecule of the first SAM.

Returning to FIG. 1, a first force is applied to the single first SAM to cross-link the SAM (112). In one embodiment, the first force is UV irradiation or electron beam. In one embodiment, the first force is UV irradiation. In one embodiment, UV irradiation may cross-link the first SAM to further stabilize the first SAM.

In one embodiment, a single and stable SAM layer forms after the application of the first force.

In one embodiment, steps 106-112 may be repeated to form a multiple layer of the SAM (114).

For example, the first solution may be applied to the second liquid surface of the first SAM to form a second SAM with a third liquid surface over the first SAM.

In one embodiment, the first solution may be applied to the second liquid surface of the first SAM by using a device such as a syringe, a needle, a pipette or similar so that at least one characteristic of the second SAM can be controlled.

In one embodiment, the at least one characteristic includes shape, size, the amount and others.

In one embodiment, two or more characteristics can be controlled. For example, both shape and size of the second SAM can be controlled.

For example, a syringe, a needle or a similar device may be used to apply a suitable amount of the first solution to form the second SAM at least in a controllable shape or size.

Subsequently, the second solution is applied on the third liquid surface to form a fourth liquid surface over the second SAM.

Similarly, a syringe, a needle or a similar device may be used to apply a suitable amount of the second solution on the third liquid surface to form a fourth liquid surface over the second SAM at least in a controllable shape or size.

A similar first force such as UV irradiation or electron beam may be used to cross-link and further stabilize the second SAM at least in a controllable shape or size.

A similar process of steps 106-112 may be repeated until ideal multiple layers of the SAM are produced (114). The ideal multiple layers of the SAM have at least one controllable characteristic such as shape or size during the process. As such, a 3D structure with controllable shape or size may be produced.

As shown in FIG. 1, after the formation of the multiple layer of the SAM, either a second force is applied to anneal the multiple layers of the SAM to form a soft material (116) or a third force is applied to anneal the multiple layers of the SAM to form a hard material (118). Thus, a 3D structure is produced.

In one embodiment, the second force and the third force are heat.

Figure 2:
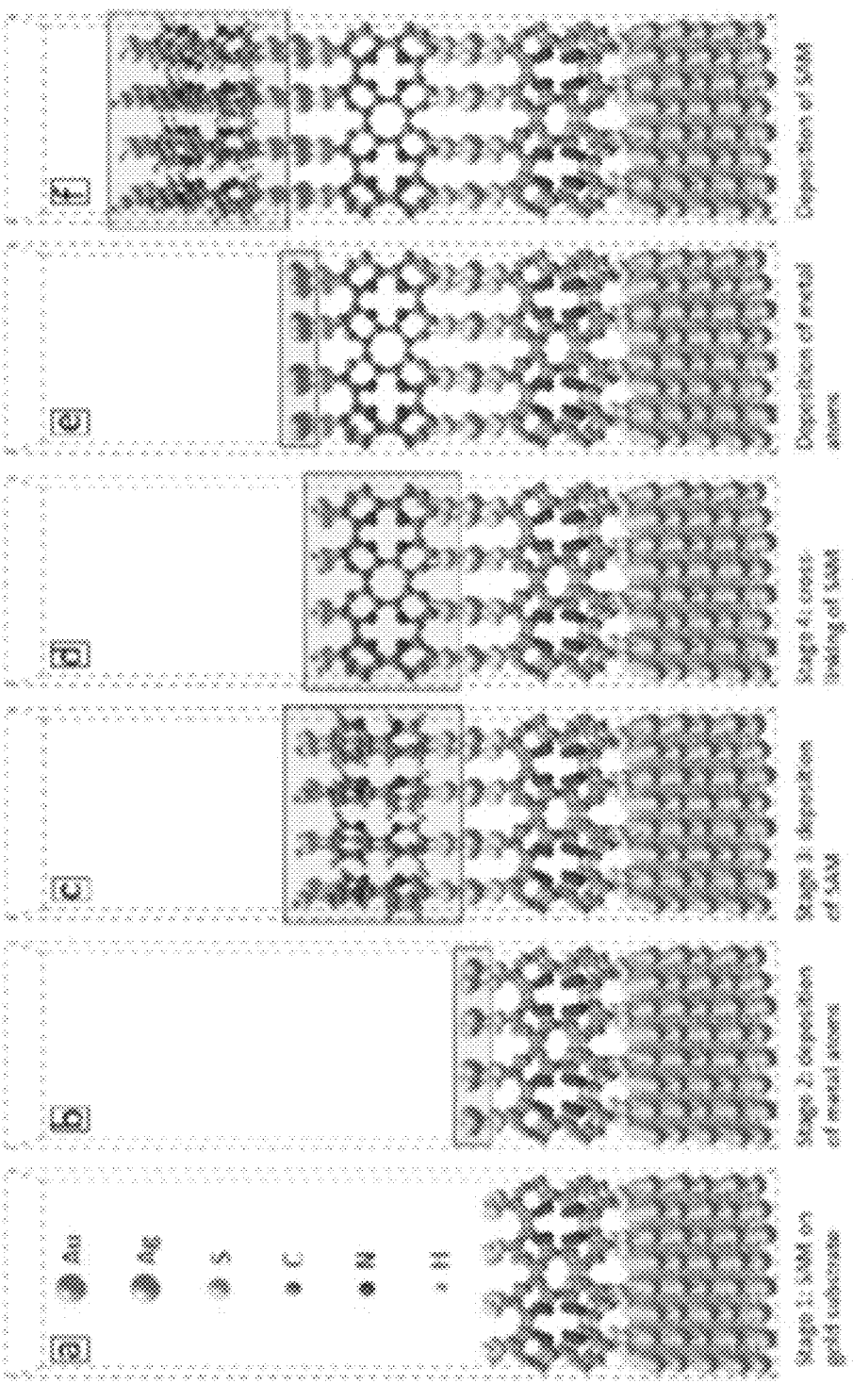
FIG. 2 is a set of diagrams showing creating 3D structures using SAM of dithiol-group molecules on gold substrate according to certain embodiments of the present disclosure.

Turning to FIG. 2, a systematic diagram showing formation of multiple layers of SAMs is depicted.

For example, in FIG. 2, an Au substrate is used. A dithiol dipyridine is used as an exemplary SAM molecule. Silver (Ag) is used as exemplary metallic atoms or particles.

As shown in FIG. 2*a*, during stage 1, a first SAM forms on the Au substrate with one of the thiols attached to the Au surface. One free thiol of the dithiol dipyridine is open for attachment after the stage 1.

As shown in FIG. 2*b*, during stage 2, silver atoms are deposited and attached to the free thiols of the dithiol dipyridine of the first SAM.

FIG. 2c shows that a second SAM forms on the top of the first SAM with one thiol of the second SAM is attached to the silver atoms of the first SAM. This is stage 3.

As shown in FIG. 2d, in stage 4, the first and second SAMs are cross-linked (e.g., by UV irradiation) so that chemical bonds form between each of the dithiol dipyridines in the SAMs. As such, the first and second SAMs are stabilized.

The steps of stages 1-3 may be repeated so that multiple layers of SAM can form.

As shown in FIGS. 2e and 2f, another layer of Ag atoms may be deposited on the top of the second SAM so that a third SAM can form on the top of the second SAM.

As such, ideal multiple layers of SAMs can be produced by using the same process as discussed above.

In one embodiment, at least one characteristics of the SAM in the method is controllable. In one embodiment, the at least one characteristics of the SAM comprises shape and size. As such, a 3D structure with a controllable shape or size may be produced.

Figure 3:
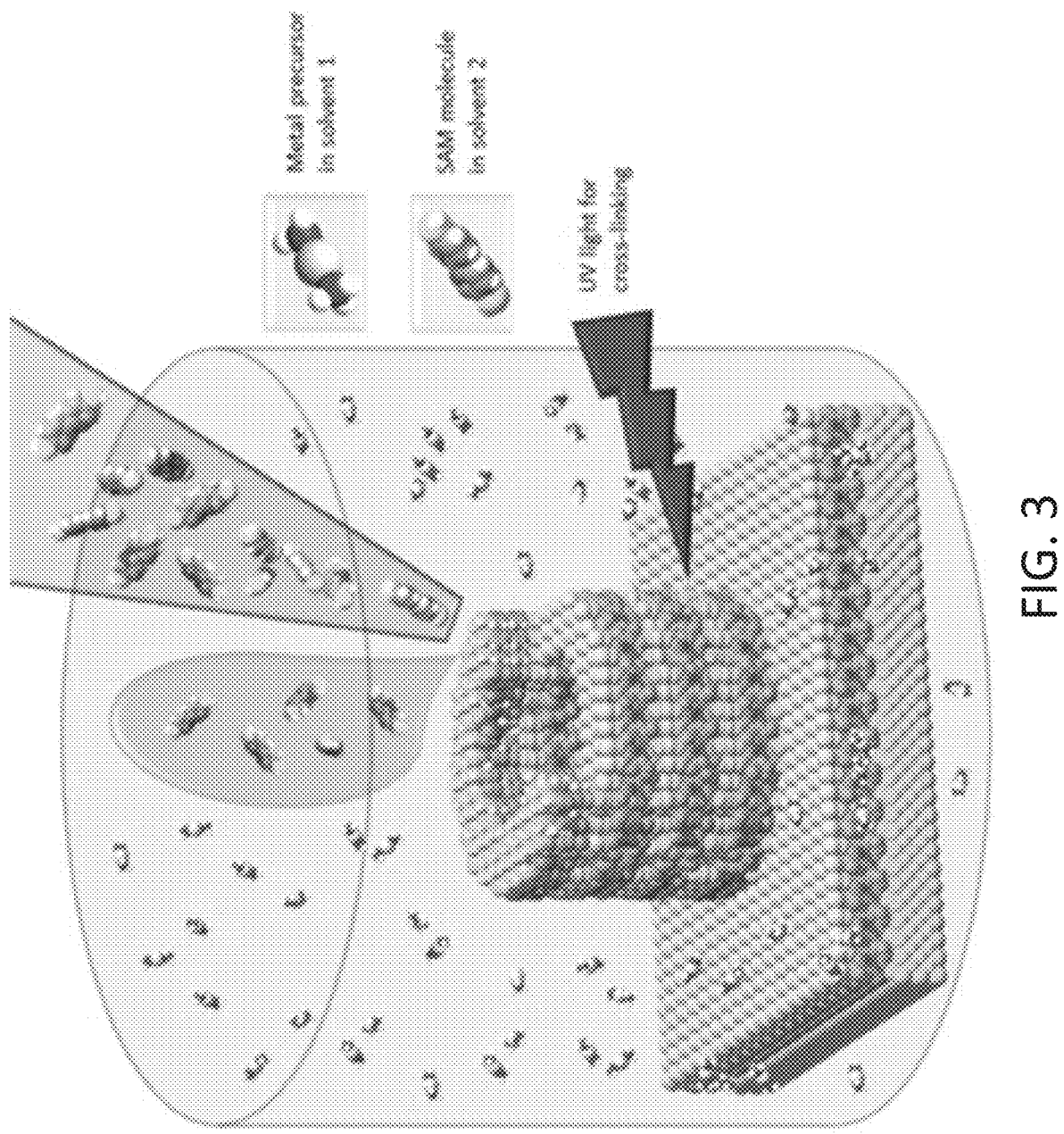
FIG. 3 is a set of diagrams showing 3D printing by using a solution-based method according to certain embodiments of the present disclosure.

Referring now to FIG. 3, a systematic diagram showing formation of a 3D structure with controllable shape and size is depicted.

As shown in FIG. 3, the whole system is immersed in an aqueous solution including Ag precursors.

As shown in FIG. 3, a thin-output device such as a syringe, a needle, a pipette or similar can be used to control the shape, the size and other characteristics of the SAMs.

In one embodiment, only the SAM molecule solution may be applied by using the thin-output device such as a syringe, a needle, a pipette or similar.

As shown in FIG. 3, after the formation of a SAM with controllable shape and size, a UV irradiation can be used to cross-link the SAM molecules to stabilize the SAM.

Referring now to FIG. 4, a systematic diagram showing another exemplary formation of a 3D structure is depicted.

As shown in FIG. 4, the whole system is immersed in an aqueous solution including Ag precursors.

As shown in FIG. 4, an Au substrate is used as the substrate. n-nonane dithiol (in n-hexane) is used as an exemplary SAM molecule. Ag atoms are used as the exemplary metallic atoms.

SAMs of n-nonane dithiol molecules are used as building blocks for forming 3D structures. As shown in FIG. 4, n-nonane dithiol molecules are self-assembled on the Au surface to form a SAM after n-nonane dithiol molecules in n-hexane are applied on the substrate.

Since the whole system is immersed into an aqueous solution containing a high concentration of Ag atoms, the surface of the first SAM will be grafted by Ag ions.

As shown in FIG. 4, following additional droplets of n-nonane dithiol molecules in n-hexane on the top of the first SAM, the metal-sulfides-carbon nanosheet by chain reaction can be produced.

The resulting silver-sulfides-carbon hybrids structures are characterized by X-ray photoelectron spectroscopy (XPS), and SEM.

Figure 5A:
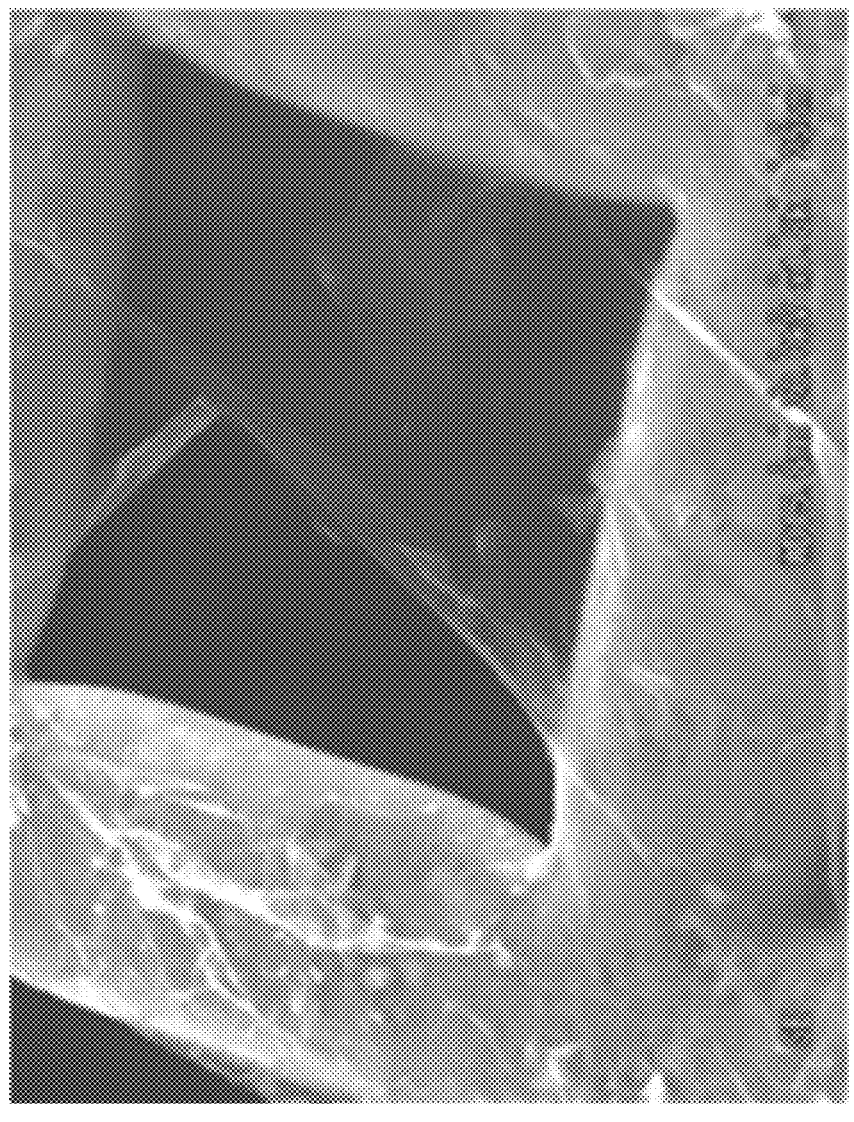
FIG. 5A-5E is a set of images and graphs showing (FIG. 5a) Atomic-force microscopy image of silver-sulfide-carbon layered structure and (FIGS. 5b-5e) XPS images.
Figure 5B:
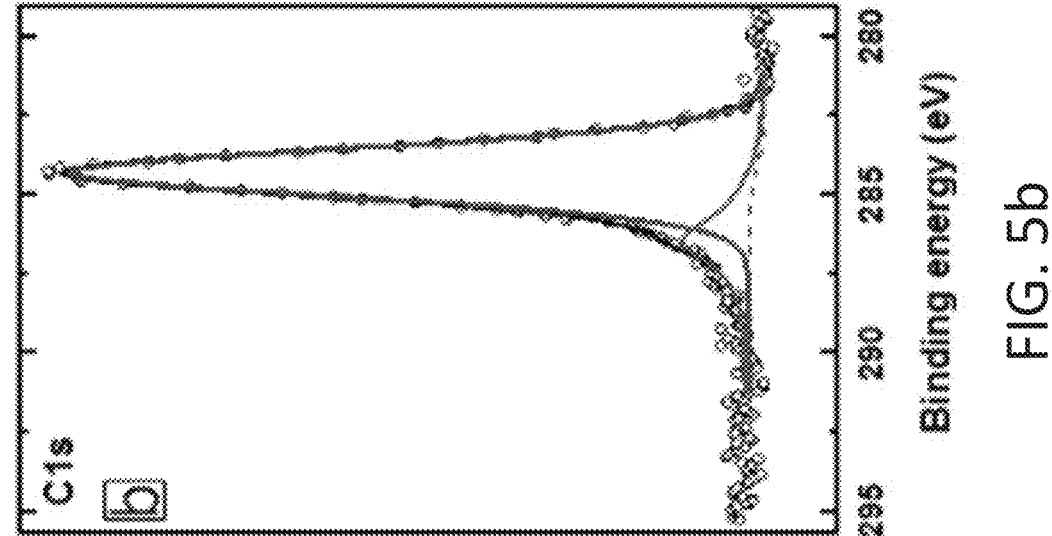
Figure 5C:
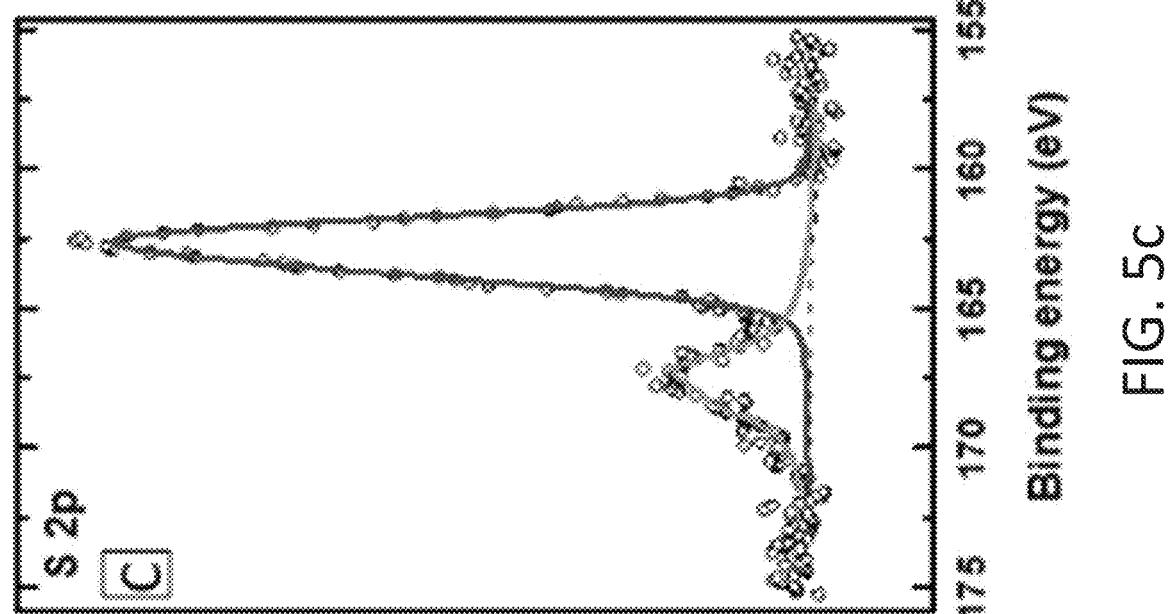
Figure 5D:
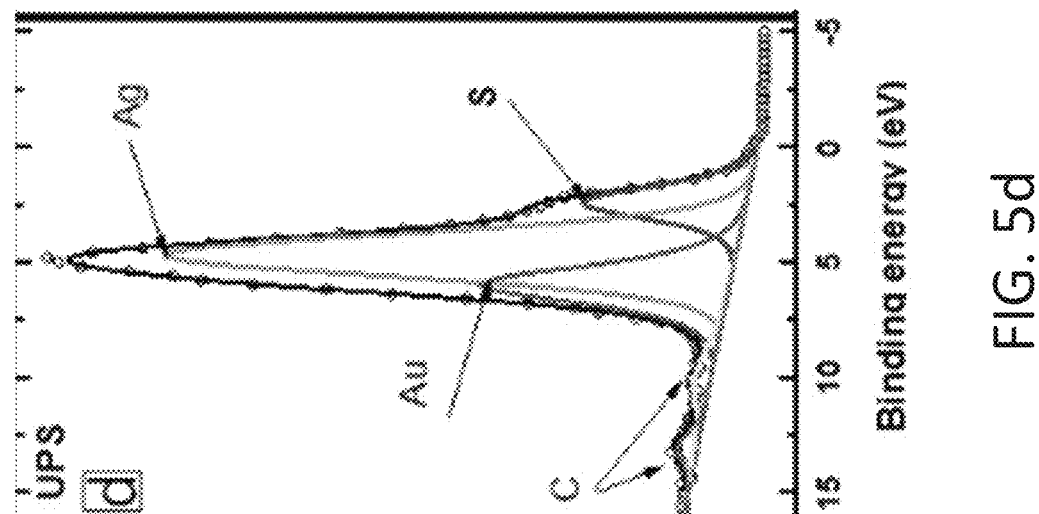
Figure 5E:
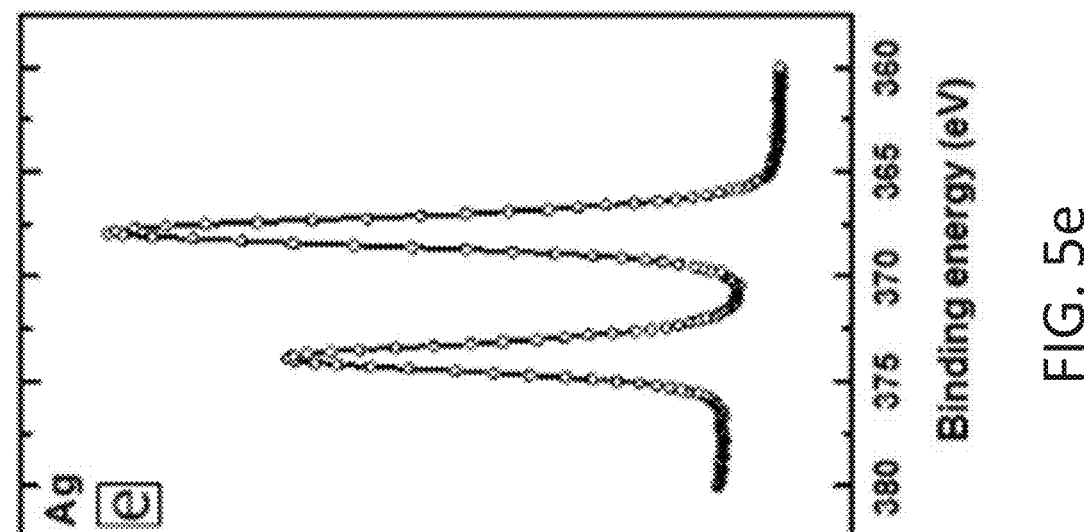

FIG. 5a shows a SEM image of the resulting 3D structure.

FIGS. 5b-5e show the XPS spectra of the obtained samples of the resulting 3D structure.

In one embodiment, metal nanoparticles may be used instead of metal atoms or ions as connecting layers for the multilayers of SAMs.

For example, metal nanoparticles such as Ag nanoparticles may be used as connecting layers for the multilayers of SAMs.

Figure 6:
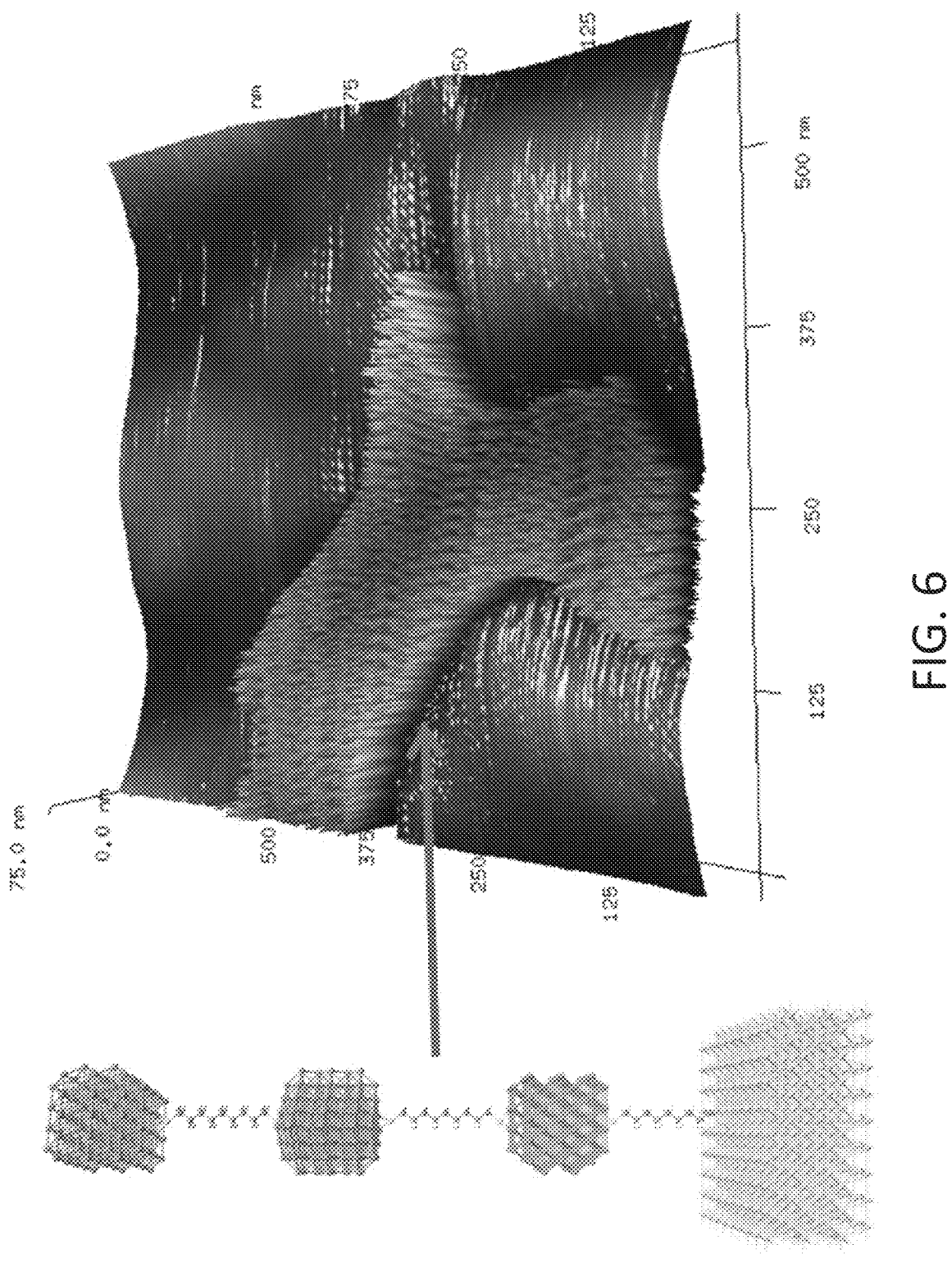
FIG. 6 is a set of image and diagram showing STM images of multilayers of C9-dithiol SAMs separated by Ni-nanoparticles.

FIG. 6 shows an exemplary 3D nanostructure under AFM images, where in the 3D structures, n-nonane dithiol SAMs are separated by Ag nanoparticles. Any metal clusters or nanoparticles can be used in constructing such metal-molecule heterostructures.

In one aspect, the present disclosure relates to a system that can undertake the method as discussed above for 3D printing.

In one aspect, the present disclosure relates to a vapor-based method (and related systems; e.g., molecular-vapor deposition method and related systems).

In one embodiment, a vapor-based method for 3D printing, comprising: providing a substrate comprising a flat surface; producing a first vapor of a self-assembled monolayer (SAM) molecule comprising a functional group at each end of the SAM molecule; applying the first vapor on the flat surface of the substrate to form a first SAM comprising a first surface; producing a second vapor of a metal precursor and applying the second vapor on the first surface of the first SAM to form a second surface; applying a first force to cross-link the first SAM; repeating steps c)-e) to form a multiple layer of the SAM; and either applying a second force to anneal the multiple layer of the SAM to form a soft material or applying a third force to anneal the multiple layer of the SAM to form a hard material.

Referring now to FIG. 8, an exemplary vapor-based method 800 for 3D printing is depicted.

As shown in FIG. 8, a substrate comprising a flat surface is first provided (802). In one embodiment, the substrate is a metal substrate such as Au. The substrate provides a space for the formation of a desired 3D structure.

A first vapor of a self-assembled monolayer (SAM) molecule comprising a functional group at each end of the SAM molecule is produced (804).

In one embodiment, the functional group is a thiol. In one embodiment, the SAM molecule is a dithiol organic molecule (an organic molecule with two thiols at each end of the molecule).

In one embodiment, the dithiol organic molecule is a dithiol alkane or a dithiol aromatic-based molecule.

In one embodiment, the dithiol alkane is dithiol hexane.

In one embodiment, the dithiol aromatic-based molecule is a dithiol dipyridine or a dithiol dibenene.

The first vapor may be produced by any suitable method such as heating. In one embodiment, the first vapor is produced by heating a solution of the self-assembled monolayer (SAM).

As shown in FIG. 8, the first vapor is applied on the flat surface of the substrate to form a first SAM comprising a first surface (806).

In one embodiment, the first vapor is applied through a switchable thin-output device such as a nozzle so that at least of one characteristic of the first SAM on the substrate can be controllable.

In one embodiment, the at least of one characteristic of the first SAM comprises shape, size, amount and others.

In one embodiment, at least two characteristics of the first SAM such as shape and size can be controlled.

As such, the first SAM with at least of one characteristic such as shape, size, amount and others is produced on the substrate.

As shown in FIG. 8, a second vapor of a metal precursor is produced and applied on the first surface of the first SAM to form a second surface (808).

In one embodiment, the metal precursor is a Ag precursor. In one embodiment, the second vapor may be produced by any suitable method such as heating. In one embodiment, the second vapor is produced by heating a solution of the metal precursor.

In one embodiment, the second vapor is applied through a switchable thin-output device such as a nozzle so that at least of one characteristic of the first SAM on the substrate can be controllable.

In one embodiment, the at least of one characteristic of the first SAM comprises shape, size, amount and others.

As such, the first SAM with at least of one characteristic such as shape, size, amount and others is produced on the substrate.

In one embodiment, at least two characteristics of the first SAM such as shape and size can be controlled.

Returning to FIG. 8, a first force is applied to cross-link the first SAM (810).

In one embodiment, the first force is UV irradiation or electron beam. In one embodiment, the first force is UV irradiation. In one embodiment, UV irradiation may cross-link the first SAM to further stabilize the first SAM.

In another embodiment, the first force is an electrical force. In one embodiment, the electrical force may cross-link the first SAM to further stabilize the first SAM.

A similar process of 806-810 may be repeated until ideal multiple layers of the SAM are produced (812). The ideal multiple layers of the SAM have at least one controllable characteristic such as shape or size during the process. As such, a 3D structure with controllable shape or size may be produced.

As shown in FIG. 8, after the formation of the multiple layer of the SAM, either a second force is applied to anneal the multiple layers of the SAM to form a soft material (814) or a third force is applied to anneal the multiple layers of the SAM to form a hard material (816). Thus, a 3D structure is produced.

In one embodiment, the second force and the third force are heat.

In one embodiment, the present disclosure relates to a system capable of undertaking the vapor-based method as discussed above to print a 3D structure.

In one aspect, the present disclosure relates to a system for printing a 3D structure.

In one embodiment, the system comprises a metal substrate providing a flat surface for forming the 3D structure; a metallic tip in an electrical communication with the metal substrate and an electric source so that the metallic tip can provide an electrical force to crosslink a self-assembled monolayer (SAM); a first switchable nozzle in a fluid communication with a vapor source for a SAM molecule; a second switchable nozzle in a fluid communication with a vapor source for a metal precursor; and a heat source for annealing the 3D structure.

Figure 7:
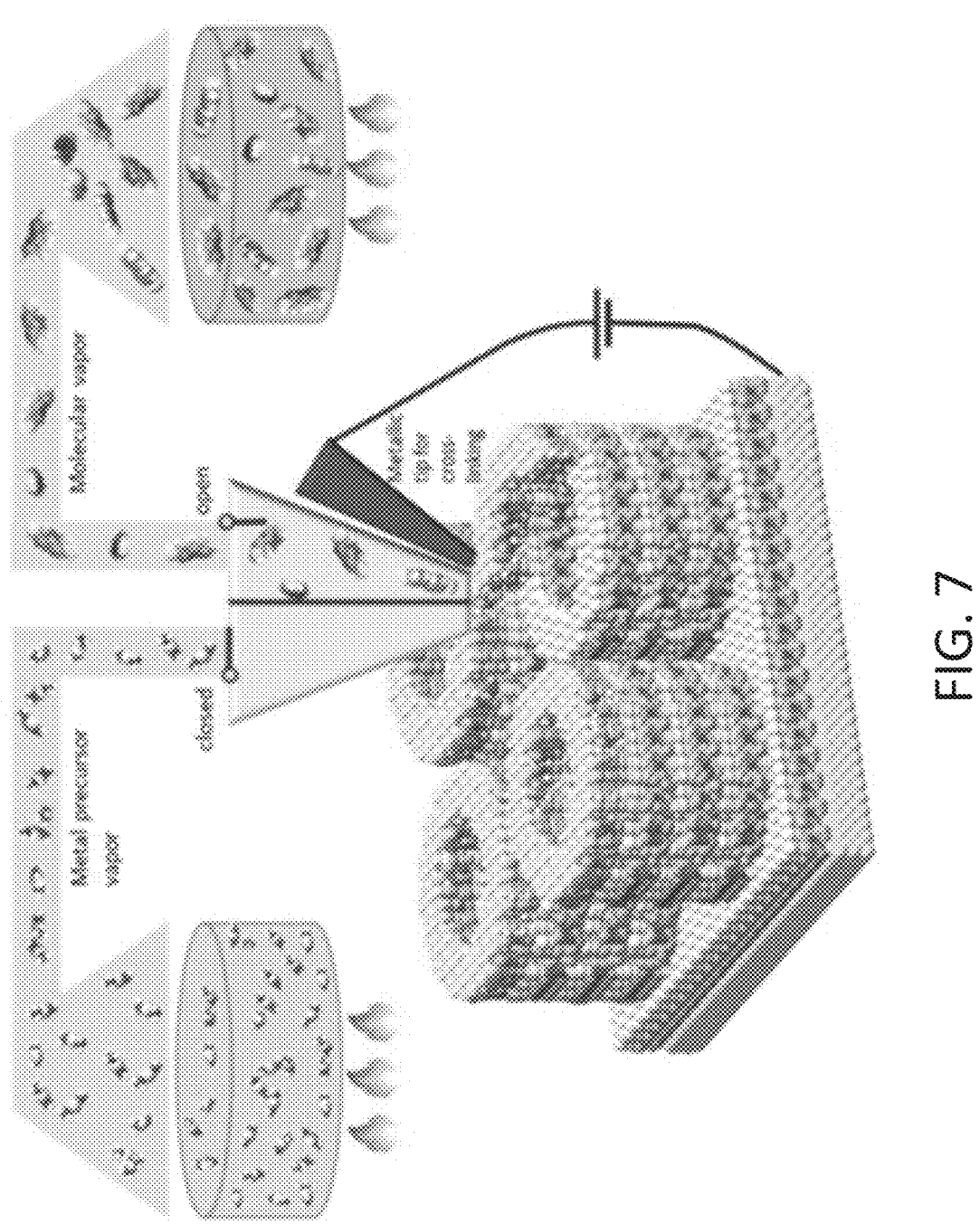
FIG. 7 is a set of diagrams showing 3D printing by using a vapor-based method according to certain embodiments of the present disclosure.

Referring now to FIG. 7, a vapor-based system for forming a 3D structure is depicted.

In one embodiment, the system comprises a metal substrate such as Au providing a flat surface for forming the 3D structure.

The system further comprises a metallic tip.

As shown in FIG. 7, the metallic tip is in an electrical communication with the metal substrate and an electric source so that the metallic tip can provide an electrical force to crosslink a self-assembled monolayer (SAM).

After formation of each of the SAMs, the metallic tip may be used to an electrical force to crosslink the SAM molecules to stabilize the SAM.

The system further comprises a first switchable nozzle in a fluid communication with a vapor source for a SAM molecule.

As shown in FIG. 7, a solution of the SAM molecule is heated to produce a first vapor of the SAM molecule, which is applied to the surface of the substrate through the first switchable nozzle.

Due to the thin output of the first switchable nozzle, at least one characteristic (e.g., shape, size and others) of the SAM may be controllable. In one embodiment, at least two characteristics such as shape and size of the SAM may be controllable.

The system further comprises a second switchable nozzle in a fluid communication with a vapor source for a metal precursor.

As shown in FIG. 7, a solution of the metal precursor is heated to produce a first vapor of the metal precursor, which is applied to the surface of the substrate through the second switchable nozzle.

The second switchable nozzle provides metal atoms or ions as connecting layers between different SAMs.

In one embodiment, the first and second switchable nozzles may be alternatively used to form multiple layers of SAMs. Thus, a 3D structure can be produced.

Further, the system comprises a heat source for annealing the 3D structure of the resulting multiple layers of SAMs.

As shown in FIG. 7, the resulting multiple layers of SAMs may be put into a heat source such as an oven to anneal the resulting multiple layers of SAMs. As such, a 3D structure can be produced.

In one embodiment, the heat of the heat source is controlled in a way so that either a soft material or a hard material can be produced. For example, a first heat force can crosslink the resulting multiple layers of SAMs to form a soft material. Alternatively, a second heat force can anneal the resulting multiple layers of SAMs to form a hard material.

Figure 9:
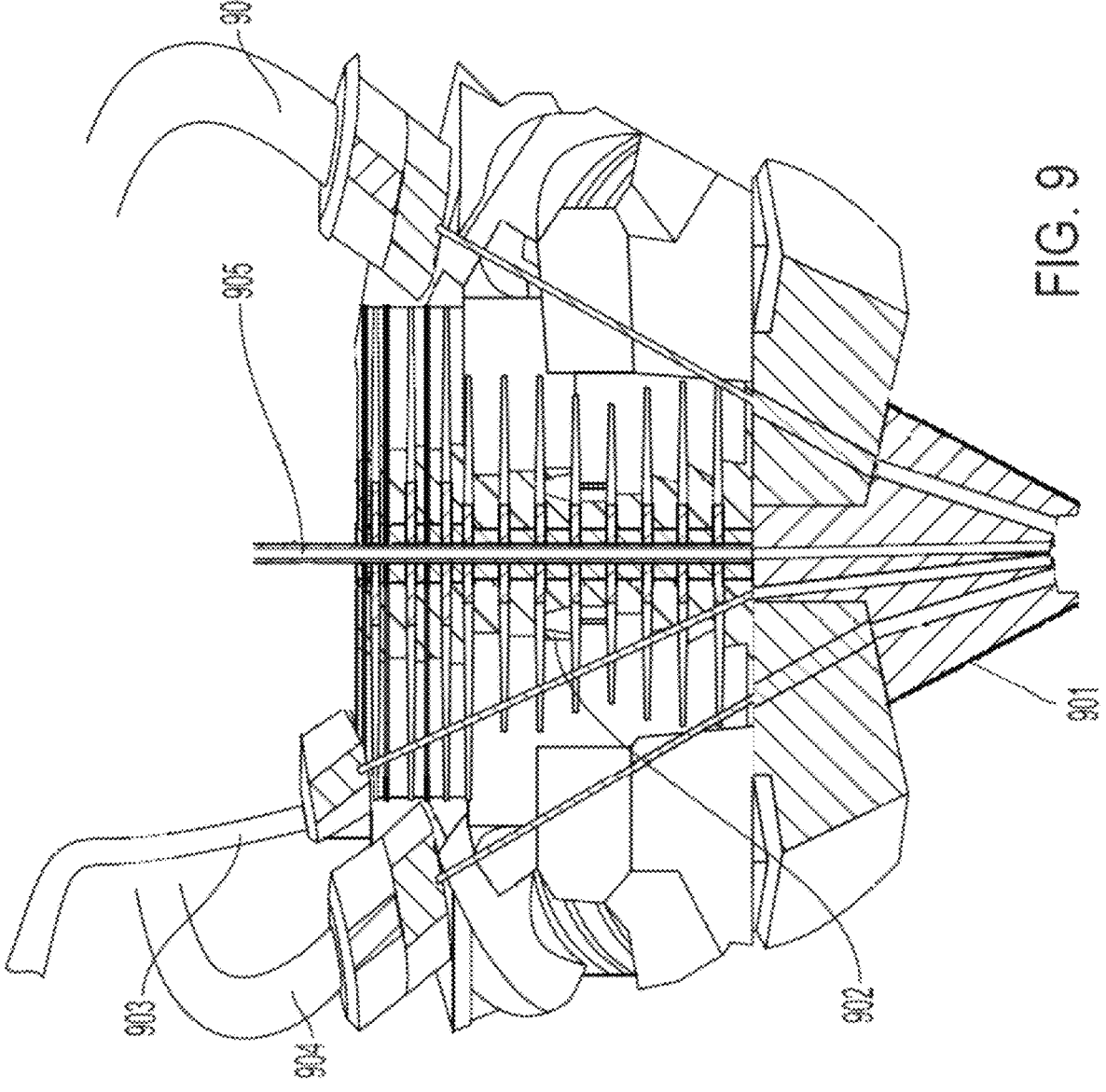
FIG. 9 is a set of diagrams showing schematics of an Air interface extruder for the self-assembly-based 3D printing according certain embodiment of the present disclosure.

Referring now to FIG. 9, an Air interface extruder for the self-assembly-based 3D printing is depicted.

As shown in FIG. 9, the Air interface extruder includes four tubes which go through a heater 902 before joining in the nozzle 901. Tube 903 is used to extrude inert gasses (e.g., Ar) to reduce the oxygen at the interface of the substrate before starting 3D printing. Tube 904 carries the active molecules for the self-assembly process. The active molecules are evaporated during passing through the heating chamber (the heater 902). The resulting self-assembled monolayer (SAM) can be cross-linked by UV radiation sent through the channel 905. The channel 905 can be a Waveguide or fiber optic capable of carrying a UV laser beam to the interface for crosslinking the SAM. This UV radiation process is needed to increase structural and mechanical stability of the SAM. Once the cross-linking process is finished, a vapor of metal atoms will be deposited through tube 906 to prepare the system for the deposition of the next SAM.

The following sections provide examples of optimization approaches from which a non-limiting example of methods and systems for 3D printing according to the present disclosure can be made. Although specific approaches are given in the sections below, the approaches provided herein do not encompass all possible options. Rather, the present inventors determined that the approaches given in the sections below represent possible approaches that can produce a suitable embodiment of methods and systems for 3D printing. It is to be understood that the methods and systems for 3D printing of the present disclosure may be made according to other approaches.

EXAMPLES

Abstract

We disclose a new approach for low-cost and morphologically stable 3D printing. The invention is based on implementing self-assembled phenomenon-based molecular building blocks, the stability of which is obtained by cross-linking the molecules either by UV radiation, or electrons. Two different strategies are proposed for the realization of such novel 3D printing: solution-based method and molecular-vapor deposition method. The present approach enables one to create new 3D complex material structures in a controlled way.

Field of the Invention

The present invention relates to a novel printing method based on molecular self-assembly for creating low-cost and new type of material for highly ordered materials fabrication and bio-applications.

Background

In general, three-dimensional (3D) printing refers to a process of creating complex 3D objects through layer by layer deposition of materials (i.e., additive manufacturing). Many different types of materials can be used for 3D printing, such as polymer and polymer compounds (acrylonitrile butadiene styrene (ABS), polylactic acid (PLA), photopolymers, polycarbonate, pristine polyamide (nylon) and glass filled polyamide, polyethylene terephthalate glycol), stereo-lithography materials (epoxy resins), ceramics, metal and metal complexes (gold, aluminum, silver, titanium and steel).

Among the plastic materials, ABS is the most common material for 3D printing and Fused Deposition Modeling (FDM) is the most suitable technology for 3D object constructions. During the FDM process, such a thermoplastic filament is heated to its melting point and then deposited layer by layer. Direct metal laser sintering (DMLS) and direct metal laser melting (DMLM) are two common technologies for metallic 3D printing. Such printers use a laser beam to melt metal powders which will consequently be deposited on top of each other. However, the processes of melting and post-deposition solidification are time consuming and therefore the speed remains an important issue in 3D printing.

In this disclosure, we present a new concept of fabricating of highly ordered and stable organic and metallic 3D structures. The concept is based on implementing self-assembled molecular building block strategy to layer by layer deposition, where each self-assembled monolayer (SAM) is separated by metal atoms or clusters. The stability of each SAM is ensured by cross-linking the molecules either by UV radiation or voltage biasing. Metallic structures can also be obtained by annealing the system composed by metallic nanoparticles intercalated with SAMs (the SAME is considered only as a binder in this case) before cross-linking to evaporate the SAMs. The proposed 3D printing can be realized using either all-solution-based device engineering method, which will radically decrease the fabrication cost, or by molecular vapor deposition technique, which enables more precise control of the resulting 3D structures. Thus, the proposed method is considered as a new category of 3D printing both in terms of processing and material.

Invention Description

General Concept

The invention relates to a concept of bottom-up manufacturing of 3D objects through layer-by-layer deposition of molecular SAMs separated by metallic atoms/clusters or nanoparticles. The details of the invention are as follows.

The proposed synthesis method is based on molecular building block strategy and consists of 5 main stages.

Stage 1. First, we create a monolayer of self assembles molecules on a metallic surface (FIG. 1), which can be obtained by immersing the metallic substrate into a solvent (e.g., n-hexane) containing the dithiol-molecules for example [1]. The molecules should have functional groups at both ends in order to: (i) immobilized in the first group to the metallic substrate and attach the second group to metallic particles or atoms (FIG. 1 illustrates SAM of dithiol molecules). The molecules will be cross linked using either UV radiation or electron beam for better mechanical stability [1].

Stage 2. In the second step, we deposit a metallic layer on top of the first SAM (FIG. 1B), which can be realized by immersing the sample into a solution with desired metal atom precursors. This metallic layer will serve as a "platform" for the next SAM.

Stage 3. In the third stage, another SAM of functional end molecules will be deposited on top of the metallic layer (FIG. 1) [2].

Stage 4. The newly deposited SAM will be cross-linked in the final stage to obtain better morphological stability (FIG. 1). Combination of ultraviolet and electron beams can be used for this purpose.

The stages 2-4 will be consequently applied to deposit more layers to the system (FIG. 1).

The optical properties (i.e., color) of each layer in the stack can be controlled by choosing specific molecules of by introducing different redox-active metal atoms which can be trapped, between, e.g., the pyridine rings of the SAMs [1,2].

Experimental Realization

We present two different experimental approaches for the experimental realization of the proposed layered structures.

Solution-Based Processed Method.

The first method is Room-temperature solution processed method which is depicted in FIG. 2. First, the metallic substrate with the first SAM (see FIG. 1) will be immersed into a solution (e.g., water) with metal atom precursors. Due to chemical reactions, the surface of the first layer will be covered with metal atoms. In the second stage, another solution (e.g., n-hexane) containing the functional end molecules suitable for creating SAMs will be injected onto the substrate through a nozzle. After the formation of the second layer, the remaining molecules will be expelled up together with the solution. The surface of the second layer will also be covered by metal atoms instantaneously. In the third step, the newly formed SAM will be cross linked using UV radiation for better mechanical properties. The last two steps will be repeated alternately to deposit the following layers. In this approach, the resolution is determined by the size of the nozzle and the shape of the object is determined by the trajectory of the nozzle and by the amount of the molecules expelled from the nozzle.

Vapor Deposition Method (FIG. 3)

In this method, vapors of metal atom precursors and molecules will be extracted from the reservoirs by heating. These vapors will be directed to a molecular extruder which will have two separate chambers. First, metal precursors will be injected to the surface two cover the surface of the first molecular monolayer. After that molecules will be injected to create SAMs. Next, the resulting SAM will be cross-linked using either UV radiation (Laser) or by applying potential difference between the substrate and the SAM using a metallic tip mounted to the extruder. These steps will be repeated alternately using the Shutters. This method is advantageous from the previous one in terms of both speed and accuracy.

Proof of Concept

We use the solution processed method to create layered carbon materials by implementing liquid-solid interface engineering. SAMs of C9-dithiol molecules are used as building blocks for our 3D structures. First, C9-dithiol molecules are self-assembled on gold surface by injecting N-hexane containing C9 molecules on the substrate (see FIG. 4). Since the whole system is immersed into water containing high concentration of silver atoms, the surface of the first SAM will be grafted by silver ions. Following droplets of N-hexane with C9 molecules result in the formation of the metal-sulfides-carbon nanosheet by chain reaction (FIG. 4).

The resulting silver-sulfides-carbon hybrids structures are characterized by X-ray photoelectron spectroscopy (XPS), and SEM. FIG. 5a shows SEM image of the resulting 3D structure. FIGS. 5b-5e show the XPS spectra of the obtained samples.

We also considered the case when the first solvent contains metal clusters rather than metal precursors. These metal particles can also be used as connecting layers for the multilayers of SAMs. This is shown in FIG. 6 where we present AFM images of the obtained 3D structures where C9-dithiol SAMs are separated by Ag Nanoparticles.

SUMMARY

A novel concept for low-cost, adaptive and mechanically stable 3D Molecular printing is proposed and confirmed experimentally. The invention is based on implementing self-assembled molecular monolayers as building blocks, where the It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCES

[1] H. Hamoudi, Z. Guo, M. Prato, C. Dablemont, W. Q. Zheng, B. Bourguignon, M. Canepad and V. A. Esaulov, On the self assembly of short chain alkanedithiols, Phys. Chem. Chem. Phys. 10, 6836-6841 (2008).

[2] H. Hamoudi, Bottom-up nanoarchitectonics of two-dimensional freestanding metal doped carbon nanosheet, RSC Adv. 4, 22035 (2014).

[3] R. Har-Lavan, I. Ron, F. Thieblemont, and D. Cahen, Toward metal-organic insulator-semiconductor solar cells, based on molecular monolayer self-assembly on n-Si, Appl. Phys. Lett. 94, 043308 (2009).

[4] H. Yamada, H. Imahori, Y. Nishimura, I. Yamazaki, T. K. Ahn, S. K. Kim, D. Kim, and S. Fukuzumi, Photovoltaic Properties of Self-Assembled Monolayers of Porphyrins and Porphyrin-Fullerene Dyads on ITO and Gold Surfaces, J. Am. Chem. Soc. 125, 9129-9139 (2003).

The invention is claimed as follows:

1. A vapor-based system for printing a 3D structure, comprising:
   a substrate;
   an air extruder comprising at least one tube, wherein the at least one tube extrudes an inert gas on the substrate, and wherein the inert gas reduces an oxygen amount on the substrate;
   a first vapor comprising an organic molecule including a functional group at each end for creation of self-assembled monolayers (SAMs) as a building block for printing the 3D structure, wherein the first vapor is configured to be applied to a surface of the substrate, and wherein the first vapor is configured to form a first SAM including a first SAM surface as a basis for the 3D structure when the first vapor is applied to the surface of the substrate;
   a second vapor comprising metal ions, wherein the second vapor is configured to be applied to the first SAM surface of the first SAM, and wherein the first vapor and the second vapor are configured to obtain molecular-metal SAMs to provide a multiple layered SAMs material when the first vapor and the second vapor are applied in repeated steps;
   a first vapor output means for applying the first vapor;
   a second vapor output means for applying the second vapor; and
   a first force output means configured to apply a first force and form the 3D structure from the multiple layered SAMs material, wherein the 3D structure is provided on the substrate, and wherein the first force output means includes at least one of a UV laser beam, a heat source, and a metallic tip in electrical communication with the substrate.

2. The vapor-based system of claim 1, wherein the organic molecule is a dithiol organic molecule.

3. The vapor-based system of claim 2, wherein the dithiol organic molecule is an alkane dithiol molecule or an aromatic dithiol molecule.

4. The vapor-based system of claim 1, wherein the metal ions of the second vapor are silver ions.

5. The vapor-based system of claim 1, wherein the substrate is a metal substrate.

6. The vapor-based system of claim 5, wherein the metal substrate includes gold.

7. The vapor-based system of claim 1, further comprising a second force output means configured to apply a second force and a third force output means configured to apply a third force, wherein the second force output means includes at least one of a UV laser beam, a heat source, and a metallic tip in electrical communication with the substrate, and wherein the third force output means includes at least one of a UV laser beam, a heat source, and a metallic tip in electrical communication with the substrate.

8. The vapor-based system of claim 7, wherein the first force is UV light, wherein the second force is heat, wherein the third force is an electric force, wherein the UV light is applied with a UV laser beam, wherein the heat is applied with a heat source, and wherein the electric force is applied with a metallic tip in electrical communication with the substrate.

9. The vapor-based system of claim 1, wherein the first vapor output means includes a first switchable nozzle, and wherein the second vapor output means includes a second switchable nozzle.

* * * * *